US007947579B2

(12) United States Patent
Jiang et al.

(10) Patent No.: US 7,947,579 B2
(45) Date of Patent: May 24, 2011

(54) METHOD OF MAKING DENSE, CONFORMAL, ULTRA-THIN CAP LAYERS FOR NANOPOROUS LOW-K ILD BY PLASMA ASSISTED ATOMIC LAYER DEPOSITION

(75) Inventors: Ying-Bing Jiang, Albuquerque, NM (US); Joseph L. Cecchi, Albuquerque, NM (US); C. Jeffrey Brinker, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 11/673,190

(22) Filed: Feb. 9, 2007

(65) Prior Publication Data

US 2007/0190777 A1 Aug. 16, 2007

Related U.S. Application Data

(60) Provisional application No. 60/772,572, filed on Feb. 13, 2006.

(51) Int. Cl.
*H01L 21/4763* (2006.01)
(52) U.S. Cl. .................. 438/485; 977/890; 438/798
(58) Field of Classification Search .......... 438/788, 438/902, 903, 485, 960, 798; 977/890
See application file for complete search history.

(56) References Cited

U.S. PATENT DOCUMENTS

| 6,875,687 | B1 * | 4/2005 | Weidman et al. | 438/623 |
|---|---|---|---|---|
| 7,135,402 | B2 * | 11/2006 | Lin et al. | 438/639 |
| 7,223,473 | B2 | 5/2007 | Jiang et al. | |
| 2003/0150811 | A1 | 8/2003 | Walter et al. | |

FOREIGN PATENT DOCUMENTS

WO 0243937 A2 6/2002

OTHER PUBLICATIONS

Riikka L. Puurunen, "Surface Chemistry of Atomic Layer Deposition: A Case Study for the Trimethylaluminum/Water Process", 2005, Journal of Applied Physics, vol. 97, pp. 1-52.*
H. Kim, "Atomic layer deposition of metal and nitride thin films: Current research efforts and applications for semiconductor device processing", J. Vac. Sci. Technol. B, 21(6), Nov./Dec. 2003, pp. 2231-2261.*
Y.B. Jiang et al, Nanometer Thick Conformal Pore Sealing of Self-Assembled Mesoporous Silica by Plasma-Assisted Atomic Layer Deposition, Journal of the American Chemical Society, Aug. 2006, vol. 128, pp. 11018-11019.*
Dow-Chemical Online, Jun. 12, 2009 <http://www.dow.com/silk/silky/small.htm>.*
H. Kim, "The Application of Atomic Layer Deposition for Metallization of 65 nm and Beyond", Aug. 19, 2005, Surface and Coatings Technology, vol. 200, pp. 3104-3111.*

* cited by examiner

*Primary Examiner* — David Vu
*Assistant Examiner* — Suberr Chi
(74) *Attorney, Agent, or Firm* — MH2 Technology Law Group LLP

(57) ABSTRACT

Barrier layers and methods for forming barrier layers on a porous layer are provided. The methods can include chemically adsorbing a plurality of first molecules on a surface of the porous layer in a chamber and forming a first layer of the first molecules on the surface of the porous layer. A plasma can then be used to react a plurality of second molecules with the first layer of first molecules to form a first layer of a barrier layer. The barrier layers can seal the pores of the porous material, function as a diffusion barrier, be conformal, and/or have a negligible impact on the overall ILD k value of the porous material.

8 Claims, 8 Drawing Sheets

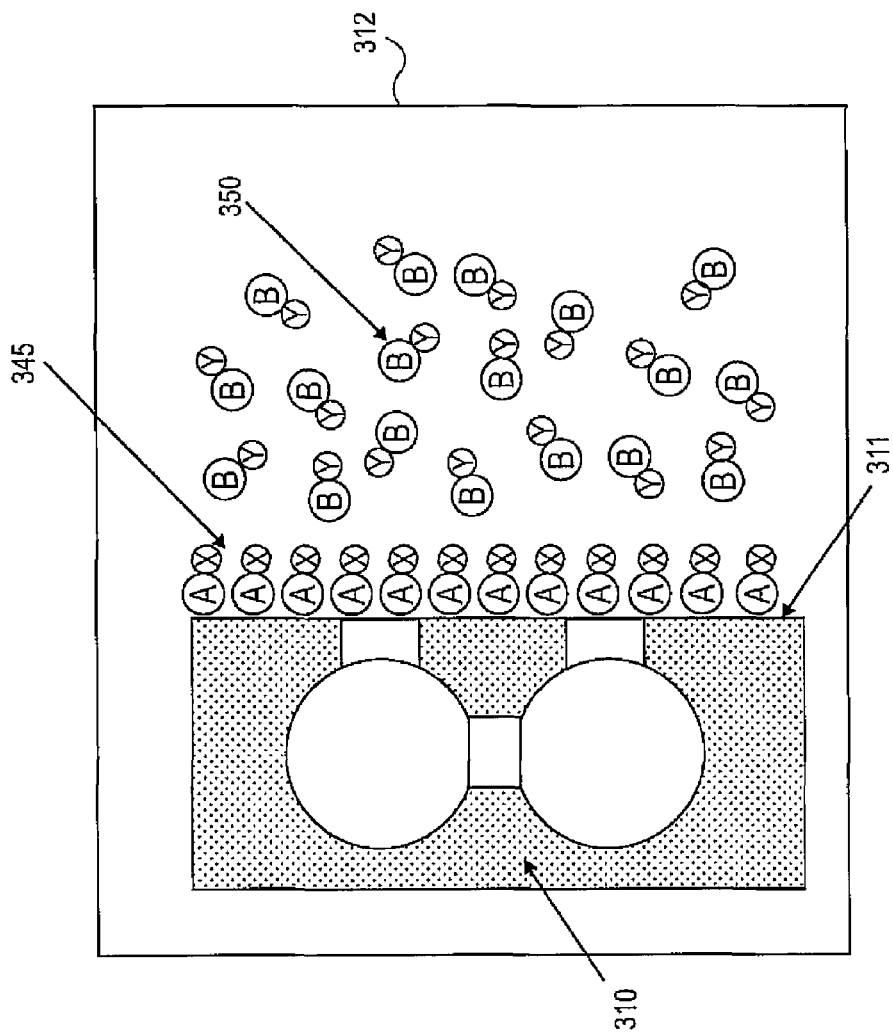
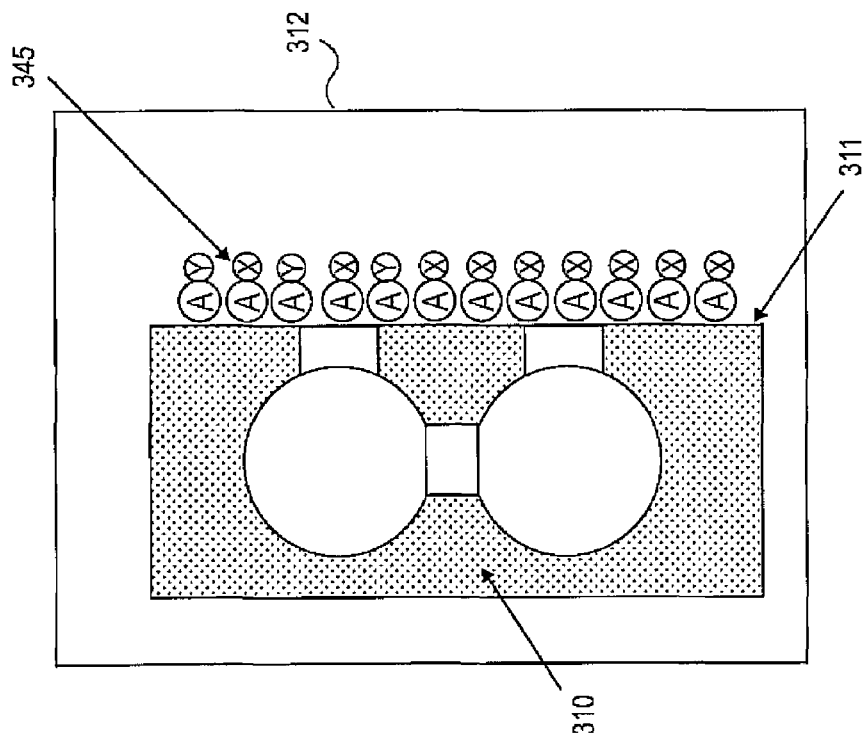
FIG. 3D
FIG. 3C

METHOD OF MAKING DENSE, CONFORMAL, ULTRA-THIN CAP LAYERS FOR NANOPOROUS LOW-K ILD BY PLASMA ASSISTED ATOMIC LAYER DEPOSITION

This application claims priority to U.S. Provisional Patent Application Ser. No. 60/772,572 filed on Feb. 13, 2006, the disclosure of which is incorporated by reference herein in its entirety.

This invention was made with Government support under Grant No. DE-FG02-0-02ER15368, awarded by the U.S. Department of Energy; Sub-Award No. 2003-08000-02 (formerly known as 04-127), awarded by the Universality of Illinois under the prime Grant No. DAAD 19-03-1-0227 awarded by the U.S. Army Research Office to University of Illinois; and developed under Contract No. DE-AC04/94AL85000 between Sandia Corporation and the U.S. Department of Energy. The U.S. Government has certain rights in this invention.

FIELD OF THE INVENTION

The present invention relates to barrier layers for use in semiconductor devices and methods for their manufacture and, more particularly, relates to barrier layers for porous materials used as interlevel dielectrics.

BACKGROUND OF THE INVENTION

As device dimensions in semiconductor integrated circuits (ICs) continue to shrink, low dielectric constant (low-k) materials are needed as interlevel dielectrics (ILD) to mitigate issues caused by reduced line width and line-to-line distances such as increasing RC-delay. To satisfy the technical requirements imposed by, for example, the microelectronics roadmap (where ultra-low k values <2 are specified), future generation ILDs will likely incorporate porous materials for use as low-k materials. However, the pores of these materials, typically on the order of angstroms to a few nanometers and connected to each other at elevated porosities, can trap moisture, gas precursors, and other contaminants in subsequent processes, making practical pore-sealing techniques essential to ultra low-k implementation.

To be useful for semiconductor integrated circuit applications, a pore-sealing coating should be conformal to the 3D topology of patterned ILD films. In addition, at the 65 nm or smaller technology node, it should be less than several nm thick so that its impact on the overall ILD k value is negligible. These requirements exclude many thin film techniques including, for example, PVD and CVD. One exception is atomic layer deposition (ALD), for which the coatings are inherently conformal and precisely controlled at sub-nm thicknesses.

Generally, ALD processes form a monolayer of precursor molecules chemically adsorbed on a surface to be coated. Then, other molecules, for example, in gaseous form, are introduced to react with that monolayer so that one atomic layer of the material desired is deposited. Normally there are several layers of molecules adsorbed on the surface. The first layer is a chemically adsorbed layer and has a strong bond with the surface. The next layers are physically adsorbed layers and are weakly bonded with each other. ALD makes use of this difference between chemical adsorption and physical adsorption. At elevated temperatures or reduced partial pressures, over broad ranges, the weakly bonded physically adsorbed molecules are removed leaving only the saturated chemisorbed monolayer on the surface. For example, the chamber can be purged by inert gas or evacuated to a low pressure, to form a saturated conformal monolayer on the sample surface. Then, the second gas is introduced to react with the precursor molecules and form an atomic layer of thin film.

Problems arise using conventional ALD on a porous substrate because conventional methods allow molecules to penetrate into the internal porosity of the ILD material, filling pores and drastically increasing the effective k value. Because ALD is a surface adsorption-based deposition process, thin film formation can take place wherever gas precursor adsorption occurs, including throughout the network of connected internal porosity. FIG. 1 depicts a cross section of a portion of a porous material 110 that includes a plurality of pores 120. Conventional ALD forms a barrier layer 130 on the surface of porous material 110, but also forms film 135 within the internal pores thereby increasing the effective k value of porous material 110. At small ILD feature dimensions, even short precursor exposure times that reduce the ALD penetration depth to, for example, 10 nm, fills a large percentage of the ILD pores.

Thus, there is a need to overcome these and other problems of the prior art to provide barrier layers and methods of forming barrier layers that are conformal and localized to the surface of a porous material.

BRIEF DESCRIPTION OF THE DRAWINGS

FIGS. 3A-F depict steps in a method for forming a barrier layer in accordance with the present teachings.

DESCRIPTION OF THE EMBODIMENTS

In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

According to various embodiments of the present teachings depicted in FIGS. 2-5B, methods for forming an ALD barrier layer localized to the immediate surface of a porous material are provided. In particular, a plasma-assisted ALD (PA-ALD) process is provided that can form a barrier layer on a porous, low-k material and seal the pores at minimal ILD thickness. As used herein, the term "barrier layer" is used interchangeably with the term "cap layer." A barrier layer formed according to the present teachings can seal the pores on a porous ILD material, function as a diffusion barrier, be conformal, localized, and/or have a negligible impact on the overall ILD k value.

Figure 1:
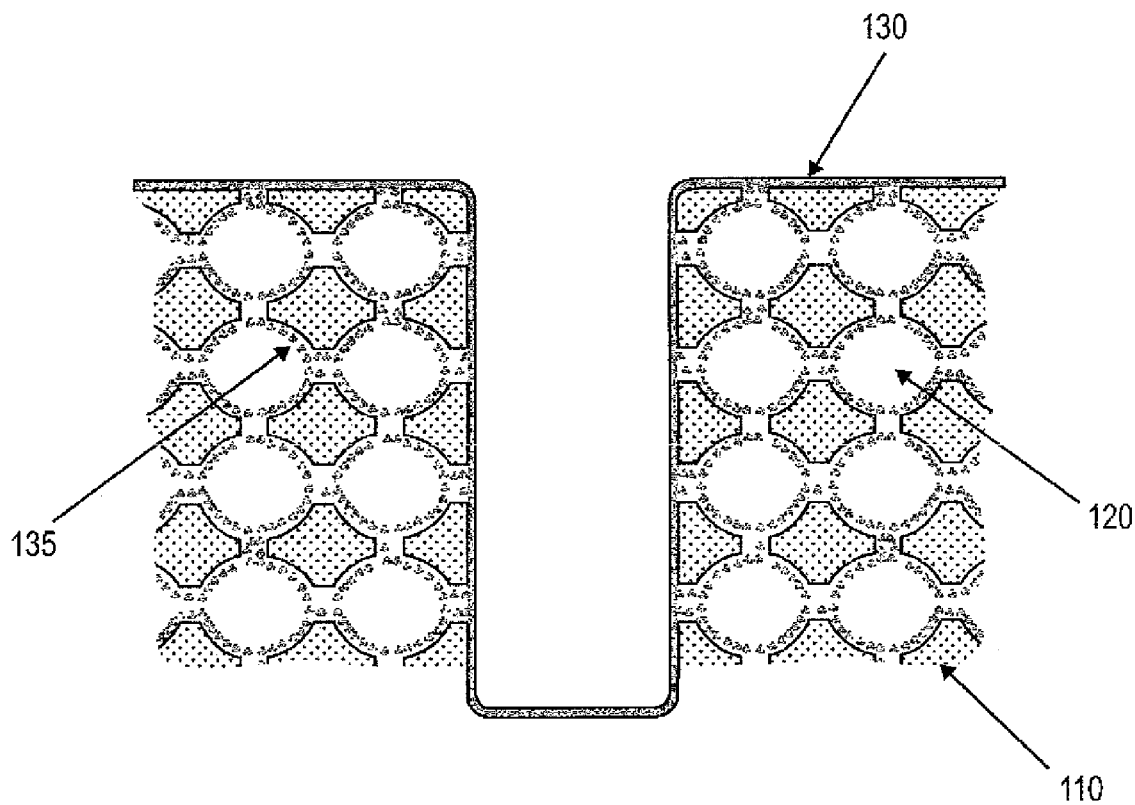
FIG. 1 depicts a barrier layer formed on a porous material by conventional ALD methods in which the internal pores are coated with film or portions of film.
Figure 2:
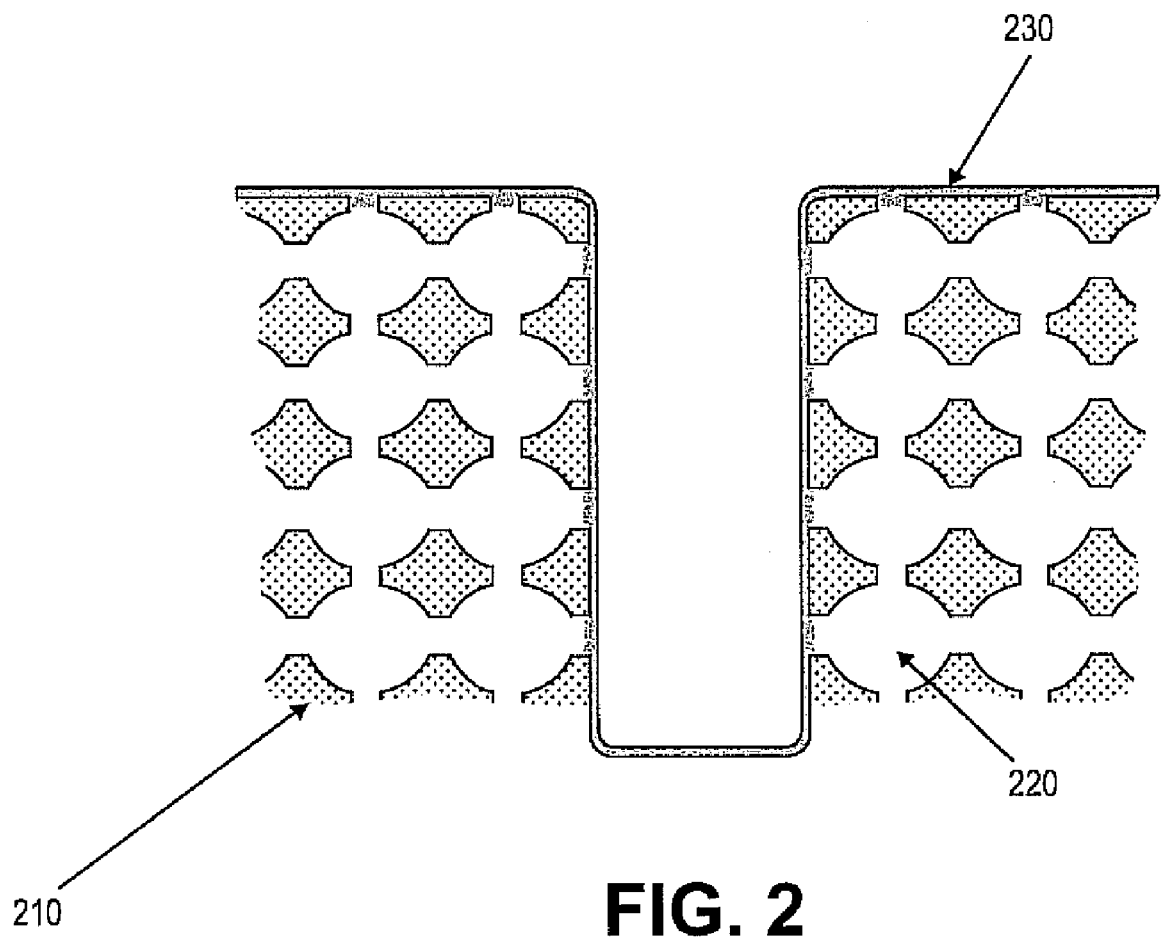
FIG. 2 depicts a barrier layer formed in accordance with the present teachings.

Referring to the cross sectional view of FIG. 2, an exemplary barrier layer 230 is shown. Barrier layer 230 can be disposed on a porous layer 210 that can include a plurality of pores 220. In an exemplary embodiment, porous layer 210 can be a low-k ILD formed of, for example, xero-gel silica or self-assembled surfactant-templated $SiO_2$. Porous layer 210 can also be $Al_2O_3$, a metal, or other porous materials know to one of ordinary skill in the art. In various embodiments, the pores can be about several angstroms to tens of nanometers in diameter and can be arranged in regular lattice like a crystal. At elevated porosities, the pores 220 can be connected to each other. Porous layer 210 can further include SD topology, for example, of patterned ILD layers. Barrier layer 230 can be a conformal layer that is confined to the surface of porous layer 210, seals the interior pores 220, and serves as a diffusion barrier. Because ALD processes can form one monolayer of the barrier layer at a time, the total thickness of barrier layer can be controlled so that its impact on the overall ILD k value is negligible.

Figure 3B:
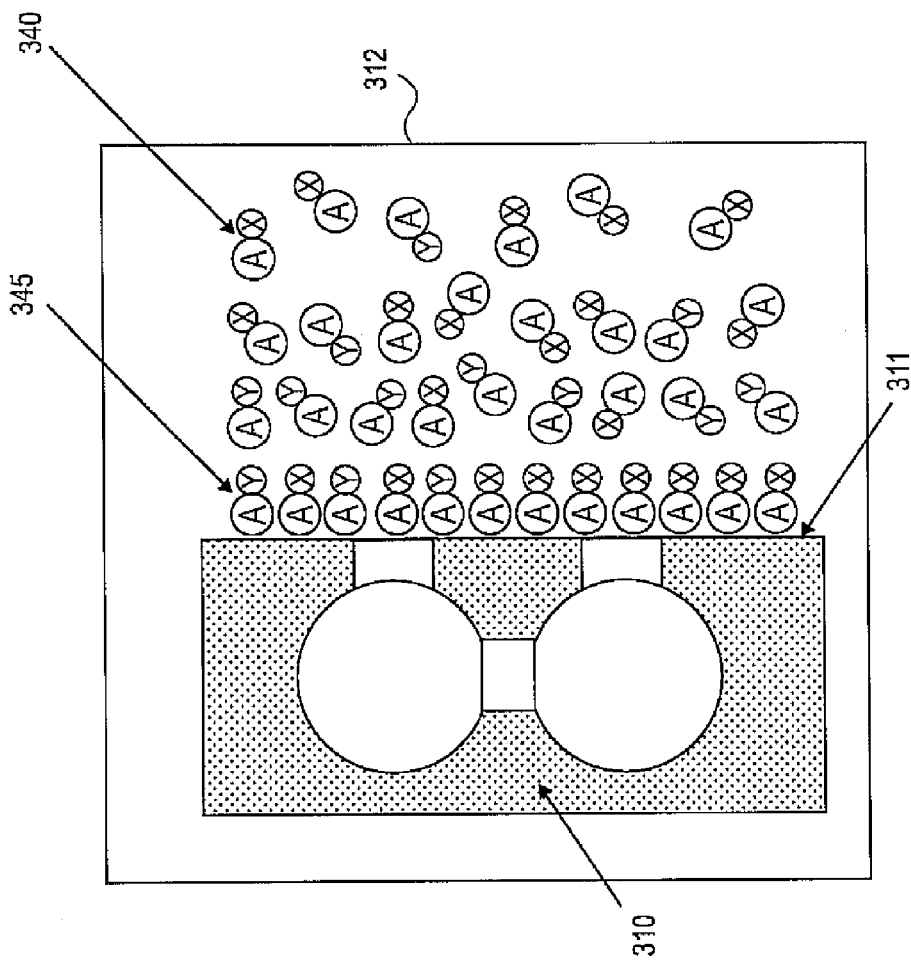
Figure 3A:
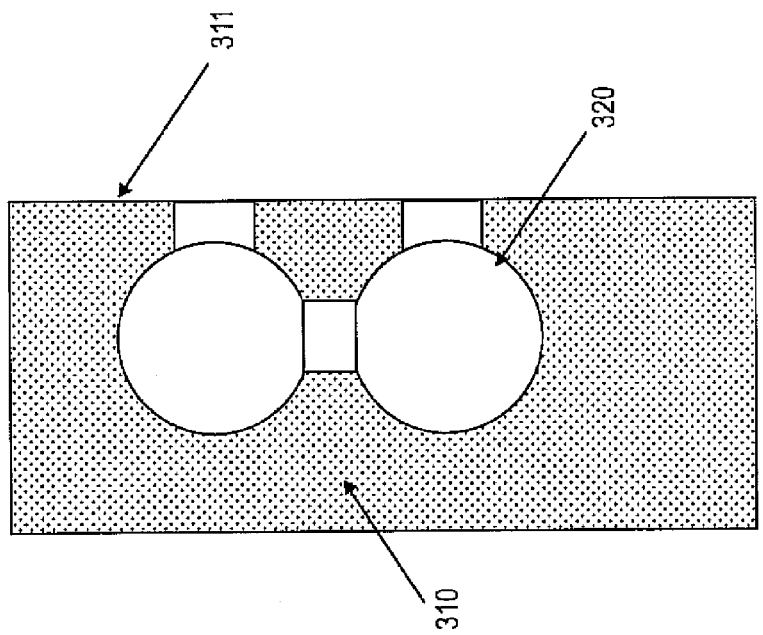

Turning now to exemplary methods for forming the barrier layers, FIGS. 3A-F schematically depict a plasma-assisted ALD process for forming a barrier layer on a porous material according to the present teachings. A portion of a porous material 310 including pores 320 and a surface 311 can be cleaned by methods known to one of ordinary skill in the art, rendering a surface as shown in FIG. 3A. Referring to FIG. 3B, porous material 310 can be placed in a reaction chamber 312 and precursor molecules 340 can be introduced. In various embodiments, precursor molecules can be gas molecules of AX. AX can be, for example, a gaseous or volatile (e.g., a volatile liquid) chemical including two or more elements or molecules that can provide one or more of the components in the objective barrier layer material. Precursor molecules 340 can adsorb onto surface 311 of porous material 310. A first layer of precursor molecules 345 can be chemically adsorbed and have a strong bond with surface 311. Subsequent precursor molecules can be physically adsorbed to first layer of precursor molecules 345, as well as weakly bonded to other precursor molecules 340.

As shown in FIG. 3C, precursor molecules 340 can be removed and substantially a first monolayer 345 of precursor molecules chemically adsorbed to porous surface 311 can remain. Precursor molecules 340 can be removed by purging the chamber 312 with an inert gas, such as, for example, Ar or $N_2$ or by evacuating the chamber 312. Referring to FIG. 3D, a plurality of reactant molecules 350 can be introduced into the chamber 312. Reactant molecules 350, for example, in a gaseous form BY can be selected to be non-reactive with precursor molecules 345 unless activated by a plasma. BY can be, for example, a gaseous or volatile (e.g., a volatile liquid) chemical including two or more elements or molecules that can react with AX under the influence of a plasma to form AB. One of ordinary skill in the art will understand that reactant molecules BY and precursor molecules AX are used for illustration purposes and that the reactant molecules and precursor molecules can be of other forms. For example, for a $SiO_2$ barrier layer, the precursor molecules can be HMDS+O2, or TEOS+O2, or other volatile organic Si— precursors that are not pyrophoric in air at room temperatures. For a $TiO_2$ barrier layer, the precursors can be Ti isopropoxide+O2, or other volatile organic Ti— precursors that are not pyrophoric in air at room temperatures. One of skill in the art will understand that other molecules for AX and BY that form a barrier layer by plasma assisted-ALD are contemplated.

In plasma-assisted ALD, ions, electrons, and radicals generally move along straight lines. Once they hit a wall, they will be neutralized and are thus no longer active. As such, plasma does not enter the nanopores and plasma-assisted ALD does not result in film deposition within the pores. Moreover, plasma-assisted ALD can be operated at room temperature further reducing film deposition within the pores. Plasma with low ion energies and a plasma source with controllable ion energy can be used to minimize sputtering of chemisorbed layers by ion bombardment.

Figure 3F:
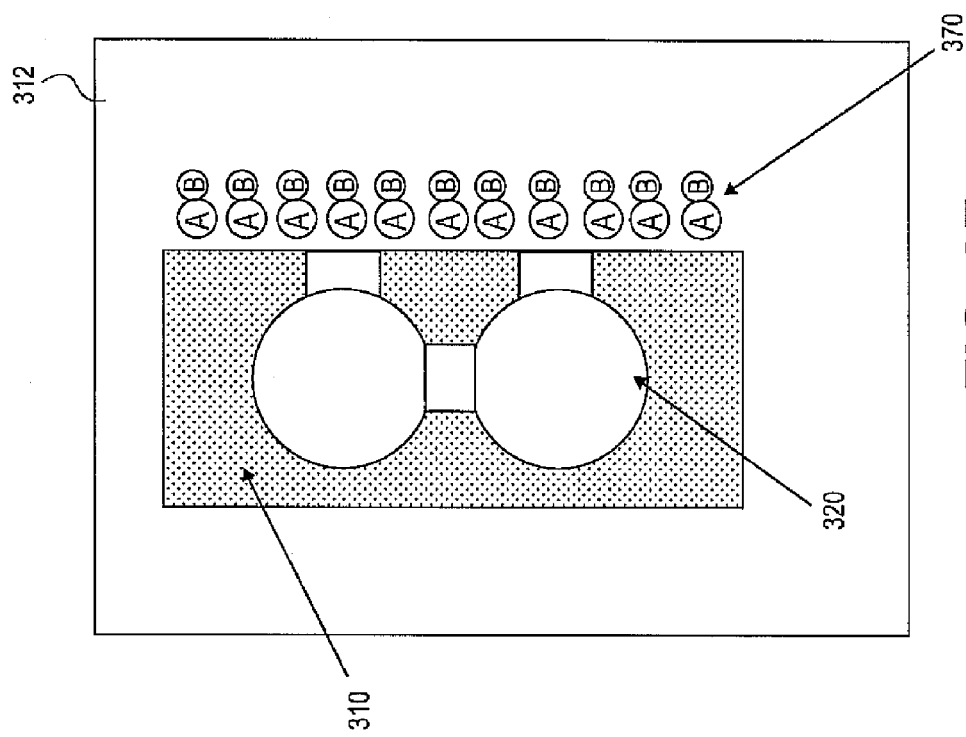
Figure 3E:
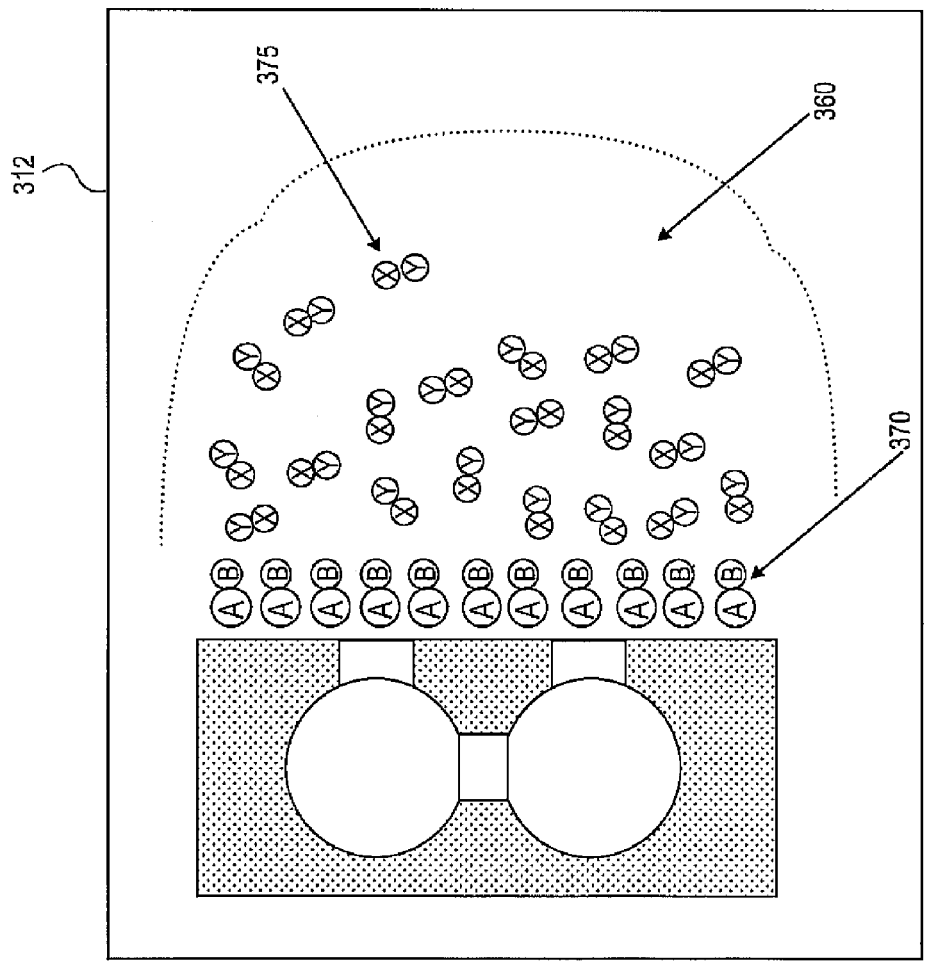

FIG. 3E shows that under the influence of a plasma 360, an ALD reaction can occur in which a barrier layer 370 can be formed of AB molecules. Molecules XY 375 can also form. Barrier layer 370 can be formed of substantially a monolayer of AB molecules, span the surface pores, be conformal to surface 311, be confined to the surface 311 of porous material 310, and/or seal the pores of porous material 310. While precursor molecules 340 can be present within the internal pores of porous material 310, they will not react with reactant molecules 350 because the plasma cannot penetrate (and ALD cannot occur) within the internal porosity. Therefore, no film or portion of film will be formed in the internal pores 320. For purposes of illustration, precursor molecules are not shown within the pores. The chamber 312 can then be purged with an inert gas or evacuated to remove the XY molecules 375 as shown in FIG. 3F. The steps depicted in FIGS. 3B to 3F can be repeated to form the desired thickness of barrier layer 370.

Exemplary methods for fabricating the barrier layers are provided below as Examples 1 and 2 and further explain use of and TEOS and HMDS.

Example 1

An exemplary plasma-assisted process in which ALD is confined to the immediate surface, allowing pore sealing at minimal ILD thickness is provided. The purpose of the plasma can be to define the location of ALD. If ALD precursors are chosen to be non-reactive unless activated by plasma, then, ALD can be spatially defined by the supply of plasma irradiation. In this regard one can recognize that the Debye length and the molecule mean free path in a typical plasma greatly exceed the pore dimension of a porous low-k material, thus plasma cannot penetrate (and ALD cannot occur) within the internal porosity.

The exemplary method was carried out in a modified plasma-assisted ALD (PA-ALD) system. The deposition chamber was a 25 mm diameter Pyrex tube, evacuated by a turbomolecular pump to a base vacuum of $5\times10^{-7}$ Torr. An RF coil surrounded the Pyrex tube for plasma generation. Samples were mounted in a remote plasma zone for reduced ion bombardment and plasma-heating effects. Oxygen and TEOS (tetraethylorthosilicate $Si(OCH_2CH_3)_4$) were used as the precursors for $SiO_2$. In the absence of plasma, they remain unreactive at room temperature. These precursors were admitted into the reactor alternately via pneumatic timing valves. A constant Ar flow of 15 sccm was used as the carrier gas as well as the purging gas.

Figure 4A:
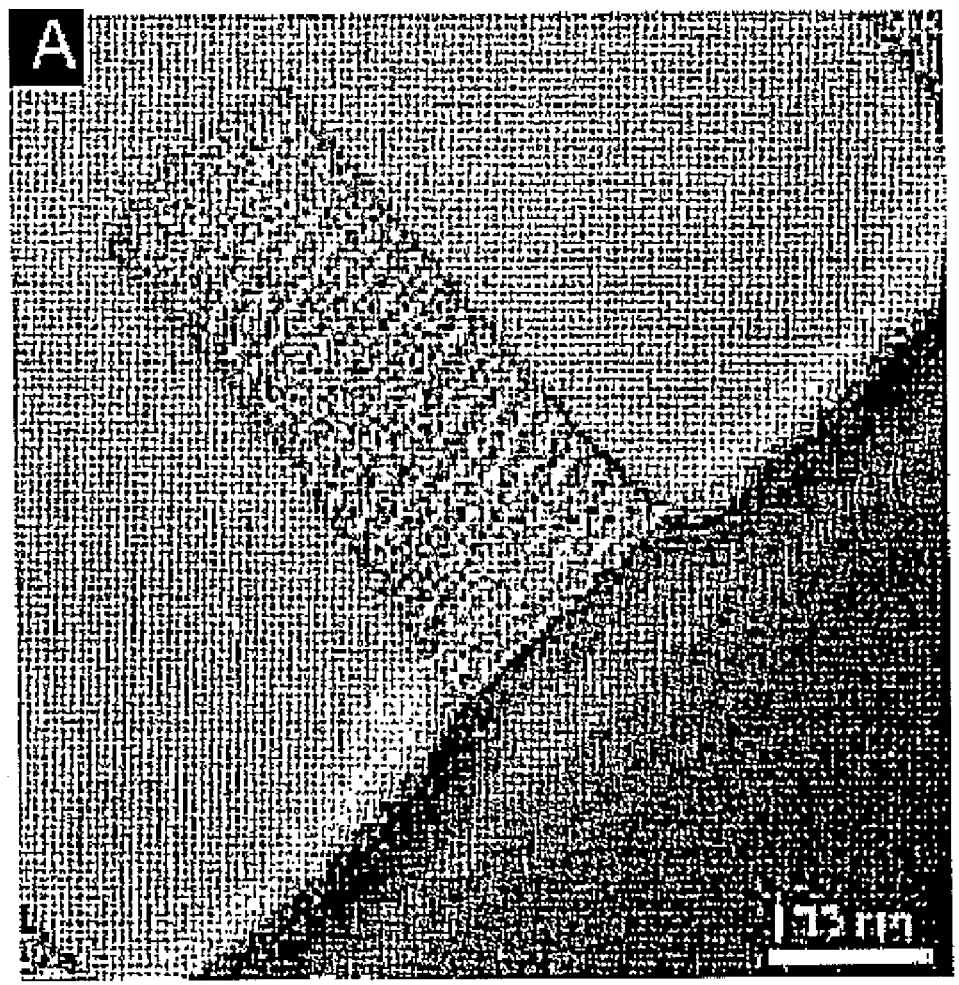
FIG. 4A is cross-sectional transmission electron microscope (TEM) image showing a conformal 5 nm thick pore-sealing coating of $SiO_2$ prepared on a patterned mesoporous low-k silica film in accordance with the present teachings.

The mesoporous silica thin film samples were prepared on silicon substrates by evaporation-induced self-assembly using Brij-56 as the surfactant to direct the formation of a cubic mesostructure characterized by a continuous 3D network of connected pores with diameters ~2 nm. These films exhibited excellent mechanical strength and thermal stability, along with an isotropic k and low surface roughness, which is important for etching or chemical mechanical polishing. At 50 volume % porosity, the k value can be 2.5 or less. Prior to PA-ALD, the samples were patterned by interferometric lithography and etched with a $CHF_3/Ar$ plasma to create 400×400-nm trenches as shown in FIG. 4A. Then the photoresist and any residual organics were removed by oxygen-plasma treatment.

Plasma-assisted ALD was performed by first introducing TEOS vapor into the reactor, followed by Ar purging to obtain monolayer (or sub-monolayer) adsorption on the sample surface. RF power was then delivered to the coil, creating an $O_2$ and Ar plasma to produce active radicals that convert surface-adsorbed TEOS into reactive silanols and may promote further conversion to siloxane. After that, the deposition chamber was purged again to remove the residual gaseous products. The above steps were repeated 150 times, with each step lasting 5 seconds.

Figure 4B:
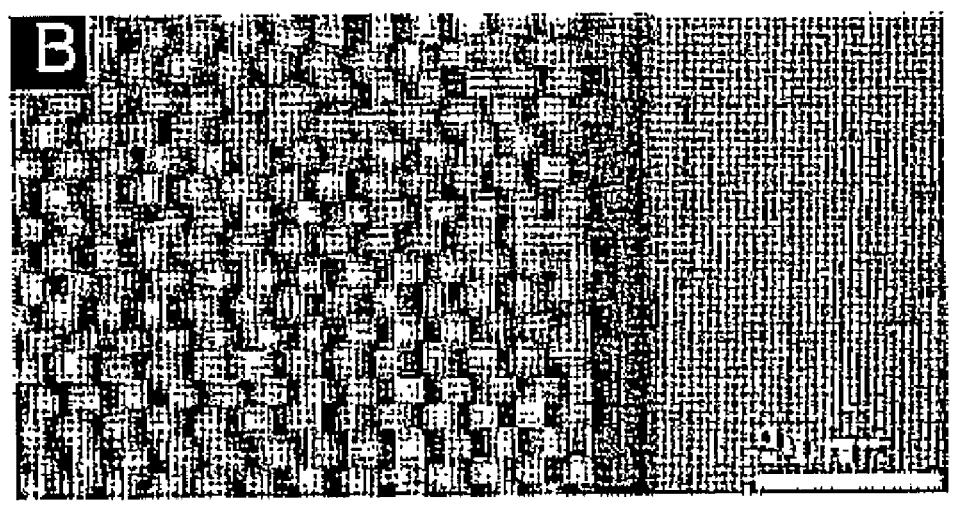
FIG. 4B is an enlarged cross-sectional TEM image showing the interface between a barrier layer and the mesoporous film in accordance with the present teachings.

FIGS. 4A and 4B show cross-sectional TEM images of the sample. A 5 nm thick $SiO_2$ coating is observed as the smooth dark rim bordering the patterned mesoporous silica feature. The coating was conformal to the patterned morphology and uniform in thickness. No penetration of the $SiO_2$ into the porous matrix was observed, and the interface between the coating and the mesoporous silica film remained sharp.

Figure 5B:
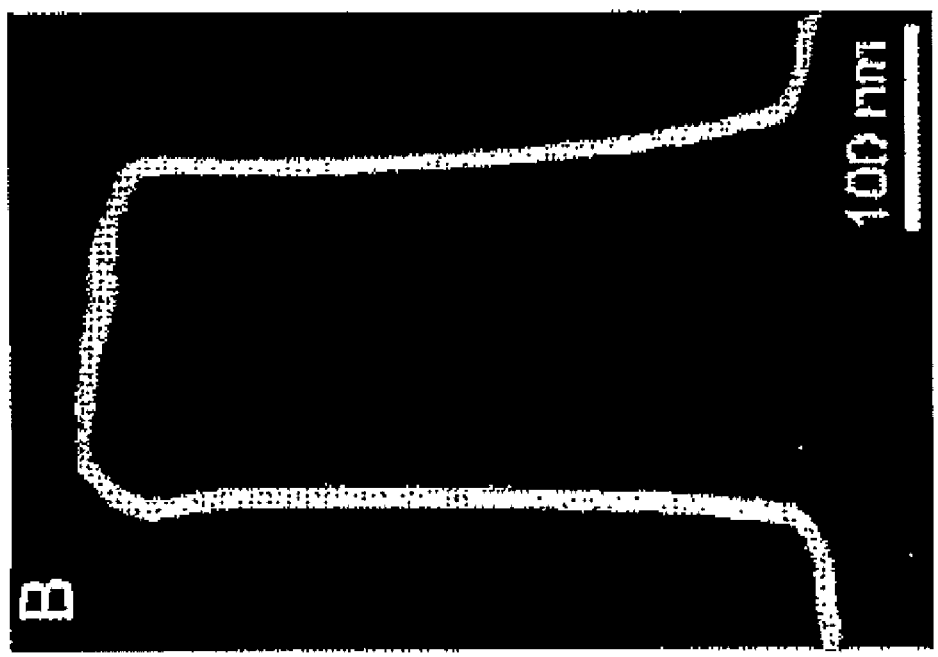
FIG. 5B is a Ti— mapping image in the same area as that of FIG. 5A acquired with an electron-energy-loss image filtering mode.
Figure 5A:
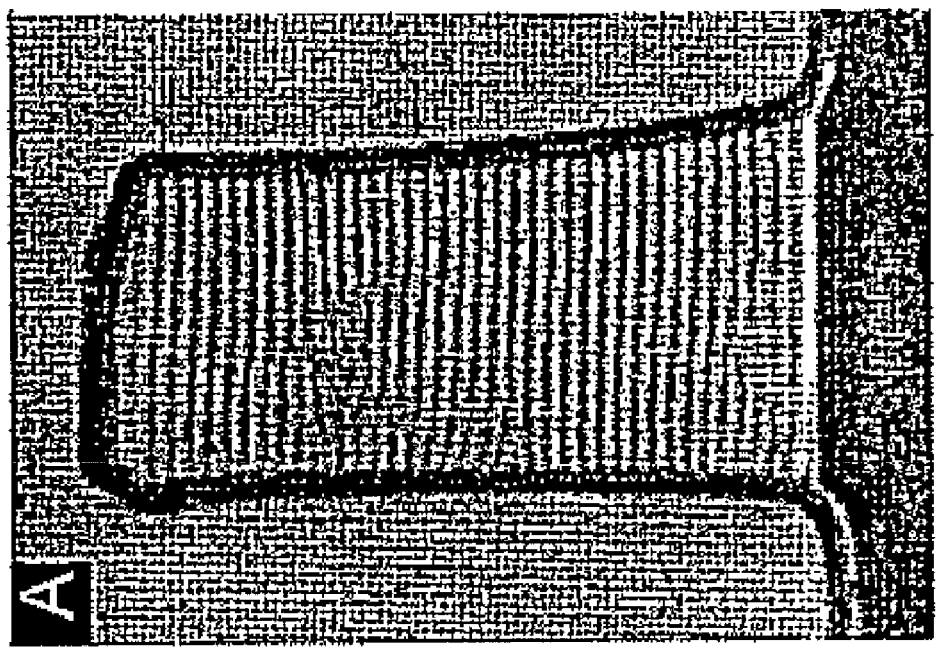
FIG. 5A is a cross-sectional TEM image showing the mesoporous sample treated by a plasma-assisted ALD (PA-ALD) pore-sealing process and then exposed to $TiO_2$ ALD conditions in accordance with the present teachings.

To verify the pore-sealing effectiveness of PA-ALD, the PA-ALD coated sample was put into a traditional thermal ALD reactor, where $TiO_2$ ALD was performed. It was shown that standard $TiO_2$ ALD will infiltrate surfactant-templated mesoporous silica, so this experiment was conducted to demonstrate the effectiveness of PA-ALD pore sealing. At 180° C., the PA-ALD coated sample was treated with 100 thermal ALD cycles using $TiCl_4$ and $H_2O$ as the precursors. FIGS. 5A and 5-B show the corresponding TEM images. FIG. 5A is a regular cross-sectional TEM image, where two ALD layers were observed. The inner, lighter layer was the PA-ALD $SiO_2$ coating, and the outer, darker layer was the $TiO_2$ thermal ALD coating. The mesoporous low-k silica appeared completely unaffected, suggesting that $TiCl_4$ and $H_2O$ cannot penetrate through the PA-ALD $SiO_2$ coating to form $TiO_2$ in the underlying porous silica matrix. This was further supported by the Ti— mapping image in FIG. 5B. The bright border in this image represented the location of Ti, and corresponded to the $TiO_2$ overlayer shown in FIG. 5A. Comparing the Ti— mapping image (FIG. 5B) to the original regular TEM image (FIG. 5A), no detectable $TiO_2$ was found beyond the PA-ALD $SiO_2$ coating. Therefore, the PA-ALD $SiO_2$ coating, although only 5 nm thick, was pinhole-free and sufficiently dense to seal the pores and protect the underlying porous low-k silica from exposure to gaseous chemicals.

Concerning the mechanism of room temperature PA-ALD of $SiO_2$, it is first noted that the deposition rate is quite low, 0.03-nm/cycle, compared to 0.07-0.08-nm/cycle for conventional $NH_3$ catalyzed $SiO_2$ ALD. Conventional ALD uses multiple water/TEOS cycles, where a water exposure serves to hydrolyze ethoxysilane bonds to form silanols, and alkoxide exposure results in condensation reactions to form siloxane bonds. As for the related solution-based 'sol-gel' reactions, hydrolysis and condensation are bimolecular nucleophilic substitution reactions catalyzed by acid or base. In PA-ALD, plasma exposure can take the place of hydrolysis, activating the alkoxide surface toward TEOS adsorption. Silanols can form during PA-ALD. However due to the monolayer (or sub-monolayer) $\equiv$Si—OH coverage, the extent of surface hydrolysis can be difficult to quantify. Additionally, the plasma can serve a catalytic role by generating nucleophilic oxo radicals, $\equiv$Si—O. that promote siloxane bond formation. At room temperature the extent of these plasma assisted hydrolysis and condensation reactions can be less than for conventional ammonia catalyzed hydrolysis and condensation reactions, explaining the lower deposition rates. Consistent with a low rate of siloxane bond formation is the highly conformal and dense PA-ALD layer indicative of a reaction-limited monomer-cluster growth process-confined, as disclosed herein, exclusively to the plasma-activated surface.

Example 2

Higher PA-ALD deposition rates can be obtained by using precursors with stronger surface adsorptions, for example, using HMDS (Hexymethyldislazane, $(CH_3)_3SiNHSi(CH_3)_3$) compared of TEOS. HMDS has stronger chemisorption on a sample surface than TEOS due to its more reactive nature to —OH groups on the sample surface as further described below.

In this example, PA-ALD was carried out with the same apparatus as depicted in Example 1, but the precursors were HMDS and oxygen. The deposition procedures were also the same as the procedures in Example 1: first introducing HMDS vapor into the reactor, followed by Ar purging to obtain monolayer (or sub-monolayer) adsorption on the sample surface RF power was then delivered to the coil, creating an $O_2$ and Ar plasma to produce active radicals that convert surface-adsorbed HMDS into reactive silanols and may promote further conversion to siloxane. After that, the deposition chamber was purged again to remove the residual gaseous products. Those steps were repeated for 60 cycles. To further enhance the step of precursor adsorption, the sample stage can be moderately heated up to 120° C. In addition, at the end of each PA-ALD cycle, the sample surface can be treated with $H_2O$ vapor to provide more —OH species for surface adsorption in the following cycle. The same cap layer as the one achieved in Example 1 was obtained in Example 2, but the deposition rate in Example 2 was about 0.106 nm/cycle, much faster than using TEOS.

Using HMDS has several advantages, including the following non-limiting examples: 1) it is easy to obtain monolayer adsorption because of its passivating —$CH_3$ final surface, thus a good PA-ALD cap layer can be attained over a broad experiment conditions; 2) HMDS is a common primer used before coating photoresist in semiconductor processing and is therefore a friendly chemical to microelectronics; and 3) HMDS has been used to cure the damaged low-k (e.g. damaged by intensive plasma during stripping photoresist).

Thus, HMDS can automatically cure the damaged low-k at the same time when sealing the pores.

As described herein, PA-ALD) can seal pores. Additionally with the demonstrated very high degree of thickness control, it is also contemplated that, prior to complete pore sealing, the pore size of the mesoporous silica can be progressively reduced in a sub-Å/cycle fashion. This combined with the thin PA-ALD layer thickness can have very important implications for membrane formation, where extremely thin inorganic films with precisely controlled pore size could enable the synthesis of robust mimics of natural ion or water channels of interest for sensors and water purification.

Figure 6:
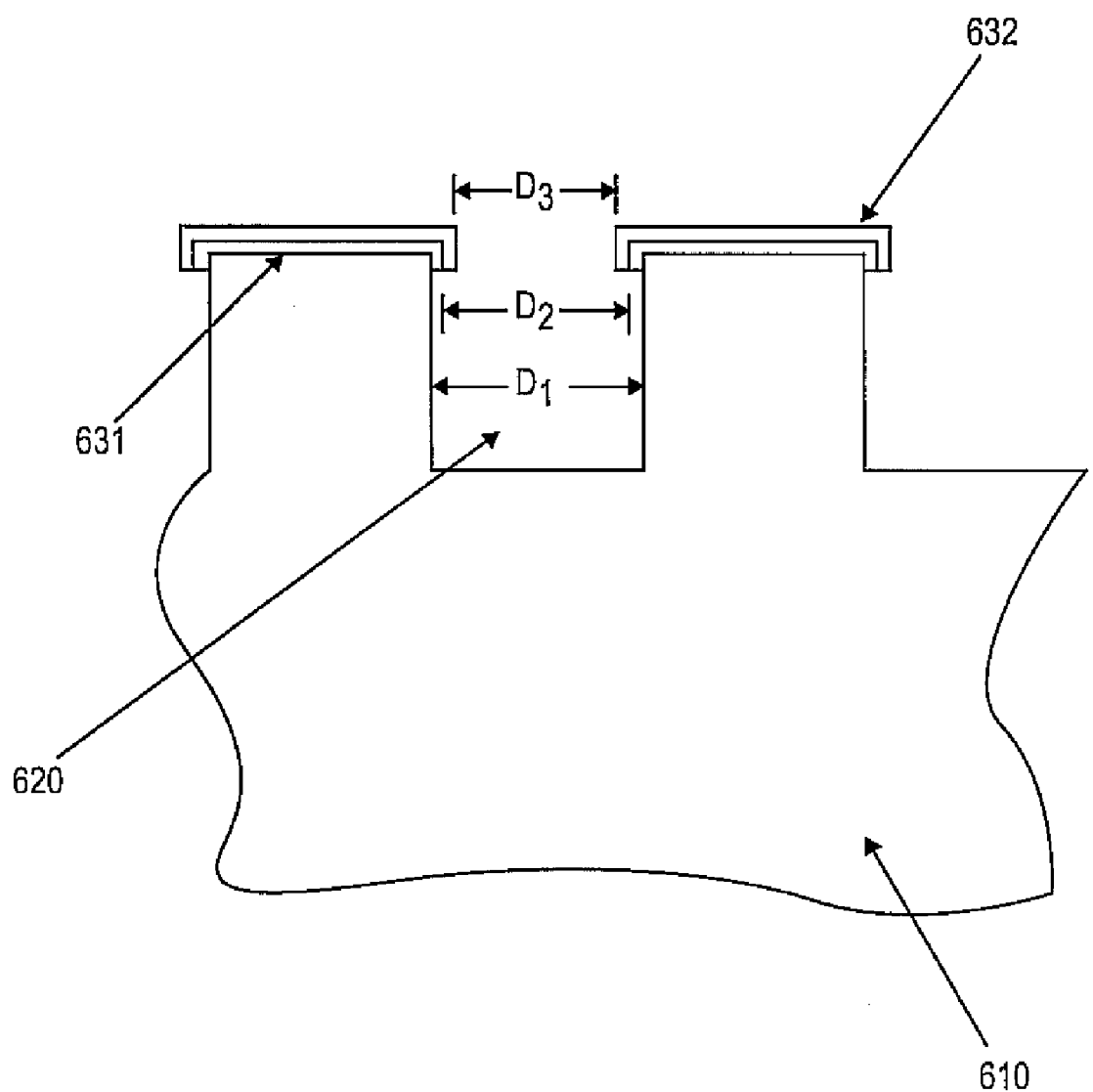
FIG. 6 is a cross sectional view of a method for reducing the diameter and/or the chemistry of pores in a porous material in accordance with the present teachings.

In another exemplary embodiment, a pore size reducing layer can be formed on a porous material to reduce the size of the pores and/or change the chemistry of the pores. FIG. 6 is a cross sectional schematic drawing of a portion of a porous material 610 that includes a plurality of pores 620 having a diameter of about $D_1$ or larger. A first pore reducing layer 631 can be formed using PA-ALD as disclosed herein. The first pore reducing layer 631 can reduce the pore diameter from $D_1$ to $D_2$, where $D_1 > D_2$. In various embodiments, a second pore reducing layer 632 can be formed using PA-ALD over first pore reducing layer 631. Second pore reducing layer 632 can further reduce the pore diameter from $D_2$ to $D_3$, where $D_2 > D_3$. According to various embodiments, first pore reducing layer 631 and/or second pore reducing layer 632 can further change chemistry in the pores. Further pore reducing layers are contemplated to reduce the pore size as desired.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for forming a barrier layer on a porous material comprising:
   using a plasma defined ALD process wherein:
   a) a plasma is used during the ALD process for localizing the barrier layer to an external surface of the porous material and without compromising porosity of the porous material;
   b) ALD precursors are selected to be non-reactive to each other unless activated by plasma, ALD deposition cannot take place unless assisted by plasma, and takes place only in places irradiated by plasma;
   c) plasma parameters comprise a Debye length and molecular mean free path each larger than a pore size of the porous material, wherein internal pores comprising the pores in the porous material are at least 5 nm below the external surface; and
   d) deposition of the barrier layer inside internal pores of the porous material is avoided and deposition takes place only on the external surface of the porous material.

2. A semiconductor device formed by the method of claim 1.

3. A method for forming a barrier layer on a porous material comprising:
   in a vacuum chamber, chemically adsorbing a plurality of first molecules on the porous material in an initially plasma-free environment, the adsorption taking place on both an external surface of the porous material and internal pores of the porous material;
   forming a first layer of the chemically adsorbed first molecules that is a monolayer or sub-monolayer on the porous material;
   choosing second molecules that are non-reactive to the first molecules unless activated by plasma, and introducing a plurality of the second molecules to the vacuum chamber; and
   generating a plasma in the vacuum chamber to activate a reaction between the first molecules and the second molecules, and converting the first layer to a first barrier layer, wherein plasma parameters comprise a Debye length and molecular mean free path each larger than a pore size of the porous material, to prevent plasma from penetrating into internal pores of the porous material, the barrier layer only formed on the external surface of the porous material, and forming the barrier layer inside internal pores of the porous material is avoided.

4. The method of claim 3, wherein forming the first layer of the chemically adsorbed first molecules that is a monolayer or sub-monolayer on the surface of the porous layer comprises removing weakly bonded first molecules by one of purging the chamber with an inert gas and evacuating the chamber.

5. The method of claim 3, further comprising:
   chemically adsorbing a second plurality of first molecules on a surface of the first barrier layer in the chamber;
   forming a second layer of the first molecules that is a monolayer or sub-monolayer on the surface of the first barrier layer; and
   using a plasma to react a second plurality of second molecules with the second layer of first molecules to convert the second layer to a second barrier layer.

6. The method of claim 5, further comprising repeating the steps of claim 4 to form additional layers of the barrier layer.

7. The method of claim 3, wherein the first layer of the barrier layer is substantially a monolayer.

8. A semiconductor device formed by the method of claim 3.

* * * * *